(12) United States Patent
Arthur et al.

(10) Patent No.: US 9,101,131 B2
(45) Date of Patent: Aug. 11, 2015

(54) SEED TREATMENT FORMULATIONS

(71) Applicant: Valent U.S.A., Corporation, Walnut Creek, CA (US)

(72) Inventors: Karen S. Arthur, Plano, TX (US); Frank Gonzales, Walnut Creek, CA (US); Michael Seitz, Reno, NV (US); Toshiya Ogawa, San Ramon, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 0 days.

(21) Appl. No.: 13/774,372

(22) Filed: Feb. 22, 2013

(65) Prior Publication Data

US 2013/0165487 A1    Jun. 27, 2013

Related U.S. Application Data

(63) Continuation-in-part of application No. 13/328,643, filed on Dec. 16, 2011, which is a continuation of application No. 12/326,309, filed on Dec. 2, 2008, now Pat. No. 8,232,229.

(60) Provisional application No. 60/991,969, filed on Dec. 3, 2007, provisional application No. 60/991,976, filed on Dec. 3, 2007, provisional application No. 60/991,985, filed on Dec. 3, 2007.

(51) Int. Cl.
| | |
|---|---|
| *A01N 25/24* | (2006.01) |
| *A01N 43/82* | (2006.01) |
| *A01N 37/22* | (2006.01) |
| *A01N 43/78* | (2006.01) |
| *A01N 25/00* | (2006.01) |
| *A01N 43/653* | (2006.01) |
| *A01N 51/00* | (2006.01) |

(52) U.S. Cl.
CPC .............. *A01N 25/24* (2013.01); *A01N 25/00* (2013.01); *A01N 37/22* (2013.01); *A01N 43/653* (2013.01); *A01N 43/78* (2013.01); *A01N 43/82* (2013.01); *A01N 51/00* (2013.01)

(58) Field of Classification Search
None
See application file for complete search history.

(56) References Cited

U.S. PATENT DOCUMENTS

| 4,981,758 | A | 1/1991 | Chu et al. | |
|---|---|---|---|---|
| 5,139,773 | A | 8/1992 | Tadros | |
| 5,674,514 | A | 10/1997 | Hasslin | |
| 6,174,988 | B1* | 1/2001 | Guth et al. | 528/319 |
| 6,448,323 | B1 | 9/2002 | Jordan et al. | |
| 2001/0008634 | A1 | 7/2001 | Anke et al. | 424/405 |
| 2004/0118040 | A1* | 6/2004 | Asrar et al. | 47/57.6 |
| 2005/0107498 | A1 | 5/2005 | Kolter et al. | 524/35 |
| 2005/0124492 | A1 | 6/2005 | Asrar et al. | 504/100 |
| 2005/0159063 | A1 | 7/2005 | Hill et al. | |
| 2005/0191390 | A1 | 9/2005 | Krochta et al. | 426/302 |
| 2006/0240983 | A1 | 10/2006 | Yamaguchi | |
| 2007/0093598 | A1 | 4/2007 | Heinrichs | 524/800 |
| 2007/0275101 | A1 | 11/2007 | Lu et al. | |
| 2007/0275985 | A1 | 11/2007 | Gebauer et al. | |
| 2008/0058450 | A1 | 3/2008 | Stimpson et al. | |
| 2008/0227646 | A1 | 9/2008 | Martin et al. | |
| 2010/0267565 | A1* | 10/2010 | Kurahashi et al. | 504/322 |
| 2011/0039694 | A1* | 2/2011 | Rosa et al. | 504/100 |
| 2011/0166022 | A1 | 7/2011 | Israels et al. | |
| 2012/0088806 | A1 | 4/2012 | Arthur et al. | |

FOREIGN PATENT DOCUMENTS

| CN | 1957701 | 5/2007 |
|---|---|---|
| EP | 0 067 479 | 12/1982 |
| JP | H01-117802 | 5/1989 |
| JP | H01-197402 | 8/1989 |
| JP | H06-239702 | 8/1994 |
| JP | 2010-536729 | 2/2009 |
| WO | WO 00/35277 | 6/2000 |
| WO | WO 2005/048707 A1 | 6/2005 |
| WO | WO 2005048707 A1 | 6/2005 |
| WO | WO2007/048730 | 5/2007 |
| WO | WO2007/093232 | 8/2007 |

OTHER PUBLICATIONS

Decision to Grant issued Jan. 15, 2013.
Sigma Catalog, 2002-2003, p. 1731.
Wesslen et al., "Preparation and properties of some water-soluble, comb-shaped, amphiphilic polymers", Journal of Polymer Science Part A: Polymer Chemistry, vol. 27, No. 12, Nov. 1, 1989, pp. 3915-3926, XP55037776.
Japanese Office Action issued Apr. 23, 2013.
International Search Report for corresponding PCT application No. PCT/US14/17360 issued May 22, 2014.

* cited by examiner

*Primary Examiner* — Sue Liu
*Assistant Examiner* — Thor Nielsen
(74) *Attorney, Agent, or Firm* — Wood, Phillips, Katz, Clark & Mortimer

(57) ABSTRACT

The present invention generally relates to aqueous seed treatment formulations comprising from about 0.2 to about 15% of at least one pesticidal agent, from about 0.1 to about 0.45% of at least one graft copolymer, at least one polyvinyl alcohol (PVA), and from about 5 to about 30% of at least one plasticizer. The present invention also relates to aqueous seed treatment formulations wherein the pesticidal agents are clothianidin, metconazole, and metalaxyl.

13 Claims, No Drawings

SEED TREATMENT FORMULATIONS

RELATED APPLICATIONS

This application is a continuation-in-part of U.S. patent application Ser. No. 13/328,643, filed Dec. 16, 2011, which claims the benefit of U.S. patent application Ser. No. 12/326,309, filed Dec. 2, 2008, and issued as U.S. Pat. No. 8,232,229 on Jul. 31, 2012, which claims the benefit of U.S. Provisional Application Ser. Nos. 60/991,969, filed Dec. 3, 2007, 60/991,976 filed Dec. 3, 2007 and 60/991,985 filed Dec. 3, 2007. The teachings of the above-referenced applications are incorporated herein by reference.

FIELD OF THE INVENTION

The present invention generally relates to aqueous seed treatment formulations that protect plant propagation material against attack by pests.

BACKGROUND OF THE INVENTION

The practice of treating seeds or other plant propagation material with pesticide formulations is well known. Insecticides and fungicides are applied to seeds to protect them from pests through the early stages of plant development in the soil. Two types of pesticide formulations are typically used: wettable powders and aqueous flowables.

Commercial seed treatment formulations require specialized equipment to properly apply them or to treat large volumes of seed. The seed treatment equipment (a seed treater) combines commercially available formulations to make slurries of pesticides. Examples of seed treaters include Gustafson Accu-Treat® RH-24 seed treater (Accu Treat is a registered trademark of Bayer CropScience), Accu-Coat HC 3000 seed treater and the like. A commercial pesticide formulation is usually formulated as a suspension concentrate. A seed treater is also used to add stickers, binders, polymers, and/or colorants to the pesticide slurry to improve handling and safety. The additives reduce dusting, and the colorants alert agricultural workers to the chemical treatment.

The number of additives and the amount of pesticide per seed that can be used in seed applications is limited by the coating and drying techniques available for use with commercial seed treating equipment. Each crop can adsorb just a limited amount of fluid, beyond which the seeds cannot be properly dried and/or handled in the seed processing equipment or planting equipment.

Furthermore, many existing formulations contain high concentrations of low molecular weight (LMW) surfactants. These LMW surfactants are typically added to stabilize the dispersion of the pesticide and to provide a stable pumpable suspension for ease of use by the treater. One of the problems associated with LMW surfactants is that they are known to increase the stress on seeds and can reduce germination.

In addition, it is known that a stable aqueous formulation is not easily obtained for certain pesticidal agents that have relatively higher water solubility and/or lower melting point. Metalaxyl (mp 63-72° C. for the technical grade, water solubility 8400 ppm) is one of such chemicals. Obtaining stable aqueous suspension formulations of metalaxyl is very challenging because there is no good way to prevent the chemical from re-crystallizing out, causing physical instability during storage.

Another problem with using ad hoc mixtures of pesticides, polymers, colorants, and other additives is the need for multiple applications to deposit and dry the desired amounts of pesticides and additives on the seeds. Multiple applications are necessary for proper adhesion.

In addition to being time consuming, the safety of these application mixtures is often unknown and problematic. Often, fillers, such as talc, are needed to reduce phytotoxicity or to improve seed drying and handling properties. As a result, handling is rendered difficult and the biological efficacy of the seed treatment is reduced.

There is still a need in the art for ready-to-use and effective non-phytotoxic all-inclusive formulations that adhere pesticides to seeds and eliminate the need to add further binders or polymers to the application mixture by a seed treater. Ideally, such a formulation can be processed in continuous flow in a single-pass application without fillers or anti-blocking powders.

SUMMARY OF THE INVENTION

The present invention provides an aqueous seed treatment formulation including: a) at least one pesticidal agent; b) at least one graft copolymer; c) at least one polyvinyl alcohol (PVA); and d) at least one plasticizer. In one embodiment, the pesticidal agents include clothianidin, metconazole, and metalaxyl.

In an embodiment the invention includes: a) from about 0.2 to about 15.0% of at least one pesticidal agent; b) from about 0.1 to about 0.45% of at least one graft copolymer; c) at least one polyvinyl alcohol (PVA); and d) from about 5.0 to about 30% of at least one plasticizer (all percentages are listed as % of 100% active materials in weight % of the total formulation).

In another embodiment, the graft copolymer may be Tersperse® 2500 (Tersperse is a registered trademark of Huntsman Petrochemical Corporation). Tersperse® 2500 is a 35% comb-branched graft copolymer solution in water.

In yet another embodiment, the PVA may be Selvol® 24-203 (Selvol is a registered trademark of Sekisui Specialty Chemicals America, LLC). Selvol® 24-203 is a 24% polyvinyl alcohol solution in water.

In another embodiment, the liquid plasticizers may be propylene glycol or hexylene glycol. In a further embodiment, the plasticizers may be a blend of propylene glycol and hexylene glycol.

In another embodiment, a solid plasticizer may be used in combination with a liquid plasticizer. Appropriate solid plasticizers include trimethylolpropane, sorbitol, urea, or any combination thereof.

In a further embodiment, the formulation may contain additional ingredients such as a preservative, an anionic surfactant, thickener, a wetting agent, a defoamer, a slip agent, a polymer emulsion, or a colorant.

In an embodiment, the preservative may be a 5-chloro-2-methyl-4-isothiazolin-3-one and 2-methyl-4-isothiazolin-3-one solution in water, such as Kathon® CG/ICP preservative (Kathon is a registered trademark of Rohm and Haas Company).

In another embodiment, the anionic surfactant may be sodium lauryl sulfate, such as Stepanol® WA-Extra (Stepanol is a registered trademark of Stepan Company). Stepanol® WA-Extra is a 30% sodium lauryl sulfate solution in water.

In another embodiment, the thickener may be xanthan gum, such as Kelzan® CC xanthan gum (Kelzan is a registered trademark of CP Kelco).

The wetting agent may be Tersperse® 4894 wetting agent in another embodiment.

In yet another embodiment, the defoamer may be Surfynol® 104PG-50 defoamer (Surfynol is a registered trademark of Air Products and Chemicals, Inc.) or Dow Corning Antifoam FG-10 or a combination of the two. In a further embodiment, Surfynol® 104PG-50 defoamer is preferred.

In another embodiment, the slip agent may be Michem® Lube 156P slip agent (Michem is a registered trademark of Michelman, Inc.) or Michem® Lube 156PFP (25% slip agent emulsion in water).

In an embodiment, the colorant may be Sunsperse® Red 48:2 colorant (Sunsperse is a registered trademark of Sun Chemical Corporation).

The polymer emulsion may be an ethylene-vinyl acetate copolymer, such as Dur-O-Set® E-200 ethylene-vinyl acetate copolymer (Dur-O-Set is a registered trademark of Celanese International Corporation), in one embodiment.

In another embodiment, the aqueous pesticide formulation may include (as 100% active materials unless otherwise specified, in weight % of the total formulation): a) from about 2.0 to about 15.0% of at least one pesticidal agent; b) from about 0.1 to about 0.45% of at least one graft copolymer; c) from about 0.5 to about 2.5% of at least one polyvinyl alcohol (PVA); d) from about 20.0 to about 30.0% of at least one plasticizer; e) from about 0 to about 0.3% of at least one preservative (as supplied); f) from about 0 to about 2.0% of at least one anionic surfactant; g) from about 0 to about 0.25% of at least one thickener; h) from about 0 to about 0.25% of at least one wetting agent; i) from about 0 to about 0.3% of at least one defoamer (as supplied); j) from about 0 to about 2.0% of at least one slip agent; k) from about 0 to about 5.0% of at least one polymer emulsion (as supplied); and l) from about 0 to about 15.0% of at least one colorant (as supplied).

In a further embodiment, the aqueous pesticide formulation may include (as 100% active materials unless otherwise specified, in weight % of the total formulation): a) about 4.25% of at least one pesticidal agent; b) about 0.35% of at least one graft copolymer; c) about 1.2% of at least one PVA; d) about 25% of at least one plasticizer; e) about 0.14% of at least one preservative (as supplied); f) about 0.40% of at least one anionic surfactant; g) about 0.14% of at least one thickener; h) about 0.176% of at least one wetting agent; i) about 0.10% of at least one defoamer (as supplied); j) about 0.75% of at least one slip agent; k) about 3.0% of at least one polymer emulsion (as supplied); and l) about 10% of at least one colorant (as supplied).

In yet another embodiment, the aqueous pesticide formulation may include (as 100% active materials unless otherwise specified, in weight % of the total formulation): a) from about 1.0 to about 12.0% of clothianidin; b) from about 0.2 to about 4.0% metalaxyl; c) from about 0.1 to about 2.0% metconazole; d) from about 0.1 to about 0.45% of at least one graft copolymer; e) from about 0.5 to about 2.5% of at least one polyvinyl alcohol (PVA); f) from about 5.0 to about 30.0% of at least one plasticizer; g) from about 0 to about 0.3% of at least one preservative (as supplied); h) from about 0 to about 2.0% of at least one anionic surfactant; i) from about 0 to about 0.25% of at least one thickener; j) from about 0 to about 0.25% of at least one wetting agent; k) from about 0 to about 0.3% of at least one defoamer (as supplied); l) from about 0 to about 2.0% of at least one slip agent; m) from about 0 to about 5.0% of at least one polymer emulsion (as supplied); and n) from about 0 to about 15.0% of at least one colorant (as supplied).

In a further embodiment, the aqueous pesticide formulation may include (as 100% active materials unless otherwise specified, in weight % of the total formulation): a) about 3.01% of clothianidin technical (97.5% active ingredient); b) about 0.907% of metalaxyl technical (97.0% active ingredient); c) about 0.454% of metconazole technical (97.0% active ingredient); d) about 0.35% of at least one graft copolymer; e) about 1.2% of at least one PVA; f) about 25.0% of at least one plasticizer; g) about 0.14% of at least one preservative (as supplied); h) about 0.4% of at least one anionic surfactant; i) about 0.14% of at least one thickener; j) about 0.176% of at least one wetting agent; k) about 0.10% of at least one defoamer (as supplied); l) about 0.75% of at least one slip agent; m) about 3.0% of at least one polymer emulsion (as supplied); and n) about 10.0% of at least one colorant (as supplied).

The embodiments of the present invention all include water in an amount sufficient to create the desired viscosity of the formulation. The balance of each formulation may be water to equal 100% by weight of the formulation.

In a final embodiment, the invention is directed to methods of preparing formulations including preparing a thickener pre-mix, preparing a metconazole and metalaxyl mixture, preparing a clothianidin slurry, and then combining the remaining ingredients, the thickener pre-mix and the metconazole and metalaxyl mixture with the clothianidin slurry. An alternate method of preparing formulations includes preparing a thickener pre-mix, preparing a slurry containing clothianidin, metalaxyl and metconazole, and then combining the remaining ingredients and the thickener premix with the clothianidin, metalaxyl and metconazole slurry.

The disclosed embodiments are simply exemplary embodiments of the inventive concepts disclosed herein and should not be considered as limiting, unless so stated.

DETAILED DESCRIPTION OF THE INVENTION

The present invention relates to formulations comprising pesticidal agents formulated to provide a ready-to-use on-farm mixture that remains stable during storage and provides for an excellent seed coating. The seed coating provides the seeds with improved protection from pests.

Applicants discovered that the ready-to-use formulations of the present invention are stable and non-phytotoxic. Formulations of the present invention are especially convenient to end users as they do not require dilution prior to application to the seeds.

The terms "plant propagation material" and "seeds" are used interchangeably throughout the specification.

The term "as supplied" means that the amount indicated by weight of the formulation ingredient is present in the claimed invention as it is provided to consumers from the manufacturer. This is in contrast to a 100% pure ingredient product.

Formulations of the present invention can be used to prepare suspension concentrates of insecticides, fungicides, and their mixtures. Disclosed formulations can be used "as is", or mixed with other additives, or diluted with water. They may be applied to seeds either by themselves or simultaneously with other pesticides or additives.

At this point, various components of the disclosed formulations will be discussed in more detail.

Pesticidal Agents

Pesticidal agents that can be used in accordance with this invention include insecticides; including but not limited to neonicotinoid insecticides like clothianidin (available from Sumitomo Chemical Co.), imidacloprid, thiamethoxam, acetamiprid, and thiacloprid; antibiotic insecticides like abamectin, emamectin benzoate, and spinosyns A and B; carbamate insecticides like bendiocarb, carbaryl, carbofuran, pirimicarb, isoprocarb, methiocarb, thiodicarb; pyrethroid insecticides like acrinathrin, deltamethrin; phenylpyrazole insecticides like ethiprole, fipronil; organochlorine insecticides like endosulfan; organophosphorus insecticides like coumaphos; diamide insecticides like chlorantraniliprole, flubendiamide; benzoylurea insecticides like bistrifluoron, chlofluazuron, diflubenzuron, flucycloxuron, hexaflumuron, novaluron, teflubenzuron, triflumuron; insect growth regulators like buprofezin; and similar classes of insecticides.

Pesticidal agents that can be used in accordance with this invention include fungicides, including but not limited to antibiotic fungicides like antimycin A1; strobilurin fungicides like azoxystrobin, dimoxystrobin, fluoxastrobin, kresoxim-methyl; carbamate fungicides like benthiavalicarb-isopropyl, carbendazim, diethofencarb, iprovalicarb, thiophanate-methyl; dicarboximide fungicides like captafol, captan, famoxadone, folpet, iprodione, procymidone, vinclozolin; triazole fungicides like bitertanol, bromuconazole, cyproconazole, diclobutrazol, difenoconazole, diniconazole, epoxiconazole, fenbuconazole, fluquinconazole, flutriafol, hexaconazole, imibenconazole, ipconazole, metconazole (available from Kureha Corp.), prothioconazole, simeconazole, tebuconazole, triadimefon, triadimenol, triticonazole; amide fungicides like boscalid, carboxin, carpropamid, dicyclomet, ethaboxam, fenfuram, fenhexamid, flusulfamide, flutolanil, furametpyr, mepronil, ofurace, oxadixyl, pyracarbolid, thifluzamide, tiadinil, zoxamide; aromatic fungicides like chloroneb, chlorothalonil; imidazole fungicides like cyazofamid, fenamidone, triazoxide; the aliphatic nitrogen fungicides like cymoxanil; morpholine fungicides like dimethomorph; pyrimidine fungicides like fenarimol ferimzone, mepanipyrim, nuarimol, pyrimethanil; pyrrole fungicides like fenpiclonil, fludioxonil; pyridine fungicides like fluazinam, fluopicolide; benzimidazole fungicides like fuberidazole, thiabendazole; dithiocarbamate fungicides like mancozeb, maneb, thiram, ziran; quinoline fungicides like quinoxyfen; aromatic fungicides like quintozene; miscellaneous (unclassified) fungicides like diclomezine, dithianon, pencycuron, pyroquilon, tricylazole; 2-[2-(2,5-dimethylphenoxymethyl)phenyl]-2-methoxy-N-methylacetamide; aromatic hydrocarbon:chlorophenyl fungicides like tolclofos-methyl; phenylamide:acylalanine fungicides like metalaxyl (available from Nufarm Ltd or LG Life Sciences, Ltd.), metalaxyl-M, benalaxyl, benalaxyl-M, and furalaxyl-M; and related types of fungicides.

The terms "insecticides" and "fungicides" are used broadly and are intended to cover all compounds active against insects and fungi. The compounds may belong to a wide range of compound classes. The pesticidal agents used in a formulation made in accordance with this invention may be a combination of the insecticides and fungicides selected to control a number of pests, insects and/or fungi, through the use of one formulation. Furthermore, it is anticipated that a formulation made in accordance with this invention may also contain auxiliary pesticidal agents that do not conform to the requirements set forth in this invention, provided that these auxiliary pesticidal agents are compatible with said formulation as determined by compatibility tests well known by those familiar with the art. For example, water-soluble pesticidal agents may be dissolved in the water carrier used in the formulation without affecting the suspension of the primary, solid pesticidal agents that are the subject of this invention. Another example of an auxiliary pesticidal agent is an encapsulated pesticidal agent, wherein, a water-insoluble liquid or low melting insecticide and/or fungicide is enveloped by a solid shell or encased in a solid matrix, and then added to a formulation described in this invention.

Mixtures of insecticides and fungicides are preferably used in the present invention. Mixtures are influenced by numerous factors such as the crop, geographic area, pest spectrum and pressure, and the prevalence of pesticide resistance.

Presently preferred pesticides in mixtures are neonicotinoid insecticides such as clothianidin; triazole fungicides such as metconazole; and phenylamide:acylalanine fungicides such as metalaxyl.

As previously mentioned, stable aqueous formulations containing metalaxyl are difficult to obtain because metalaxyl forms undesirable crystals. Applicants unexpectedly found that formulations of the present invention provide a superior solution to this known problem in the art.

Polyvinyl Alcohol (PVA)

Polyvinyl alcohol (PVA) is a water-soluble synthetic polymer. Many different grades of PVA are commercially available. While most of the available PVA polymers can be used in this invention, the preferred PVA grades have "Ultra Low", "Low", and "Medium" viscosity grades. They are usually classified by the viscosity of 4% PVA solutions. The viscosity of these PVA grades is generally between about 2.5 cP (centipoise) to about 32 cP at 20° C. The most preferred grades are the "Ultra Low" and "Low" viscosity grades.

The PVAs encompassed by the present invention have weight average molecular weights from about 12,500 g/mole to about 125,000 g/mole. Each grade of polymer has a distribution of molecular weights. The weight average molecular weight is defined as the molecular weight multiplied by the weight fraction of molecules that have that weight, summed over all the weights in the distribution, divided by the total weight. Further, the PVA polymers can be fully (98-100%), intermediately (90-98%), or partially (70-90%) hydrolyzed. Partially hydrolyzed PVA polymers are most preferred. Modified or special grades of PVA polymers can also be used. PVAs in the viscosity range disclosed above can be carboxylated or sulfonated to introduce some anionic properties that improve viscosity and dispersing power. These grades of PVA simply have some carboxylic groups ($-CO_2X$ group) or sulfonic groups ($-SO_3X$ group) added to the PVA chain, where X can be H or an alkali metal.

In a preferred embodiment, the PVA is Selvol® 24-203 polyvinyl alcohol, which is available from Sekisui Specialty Chemicals America.

Graft Copolymers

A graft copolymer is a material that has polymer chains of one chemical composition branching out from a polymer backbone with a different chemical composition. Graft copolymers that can be used in accordance with this invention include but are not limited to acrylic acid, methacrylic acid, acrylate, methacrylate or methyl methacrylate polymers which have chains of another polymer, as for example, a polyether such as polyethylene glycol, extending from the acrylate polymer backbone.

In a preferred embodiment, the graft copolymers are comb-branched polymers with an acrylic acid, methacrylic acid, acrylate, methacrylate or methyl methacrylate polymer backbone and hydrophilic polyethylene glycol (PEG) branches extending from this backbone. In two-dimensional representations, the PEG branches are drawn perpendicular to the acrylate polymer backbone (usually linear) and resemble the teeth of a comb, giving rise to the description "comb-branched". The comb-branched graft copolymers used in the present invention are proprietary materials; therefore, specific details of their composition and manufacture are not known to the applicants.

In a preferred embodiment, the comb-branched graft copolymer is Tersperse® 2500 (35% graft copolymer solution (available from Huntsman Corp.).

PVA-Graft Copolymer Combinations

The synergistic PVA and graft copolymer combination is a mixture of these two polymers. There are many advantages to using the PVA-graft copolymer combination.

First, the polymer combination coats the pesticidal agent used in the formulation and provides a protective layer between the pesticidal agent and the seed. This protective layer reduces any phytotoxicity that the pesticidal agent may have.

Second, water-soluble polymeric materials used in formulations of the invention provide for slower uptake and translocation of the pesticidal agent into the seeds. Prior art formulations typically used components to enhance the uptake and the translocation of pesticidal agents into the seeds. However, quick uptake can exacerbate any toxicity that the surfactant or the pesticidal agent may possess, resulting in a decrease in germination.

In addition, the PVA-graft copolymer combination is very water-soluble and safe on seeds. Seeds coated with the film formed by the formulations of the present invention can easily be re-hydrated by soil moisture. The film does not function as a limiting factor in the transport of moisture into seeds. The seeds' normal lipophilic layers are preserved and remain the controlling factor in moisture uptake by the seeds. Accordingly, good seed germination and coating adhesion are maintained.

Furthermore, the PVA-graft copolymer combination is compatible with dispersant systems employed in many commercial polymer emulsions. This compatibility permits the incorporation of polymer emulsions directly into the seed treatment formulation at the point of manufacture without loss in stability.

Plasticizers

As used herein the term "plasticizer" refers to a substance that is used to modify the film produced by the formulations, to allow faster drying, and to impart greater moisture sensitivity without the need for tack that can impair the flow of the seed in handling and planting equipment.

Liquid plasticizers that can be used in accordance with this invention are generally low molecular weight alkyl glycols or polyols (diols or triols), wherein the alkyl group is from 2 to 6 carbons in length. Preferred liquid plasticizers include propylene glycol and hexylene glycol.

A solid plasticizer can also be used in combination with the liquid plasticizer. Specific examples of suitable solid plasticizers include but are not limited to trimethylolpropane, sorbitol, urea, or any combination thereof. It is presently preferred to include a blend of liquid and solid plasticizers. Such a blend may include propylene glycol, hexylene glycol, urea, and trimethylolpropane.

Polymer Emulsions

When adhesion requirements are high or when high coverage is desired, polymer emulsions (or latexes) based on polyvinyl acetate and/or ethylene vinyl acetate copolymers may be added to improve adhesion and seed appearance.

An advantage of formulations of this invention is that they are "all-inclusive", i.e. they allow for adding the polymer emulsions at the point of manufacture of the formulations, as opposed to adding them at the application site. Thus, package stability is not sacrificed and moisture uptake of seeds is not adversely affected.

Polymer emulsions that may be used in formulations of this invention are stabilized by PVA and thus, are PVA-compatible. The polymer emulsions may be added to formulations without causing "dispersant shock" that can result in an undesirable increase in viscosity or gelling. Further, because the stabilizing agents for formulation suspensions and polymer emulsions or latexes are similar, no dispersant is stripped off the latex particle or the pesticidal agent particle when they are mixed together. As a result, a stable, low viscosity mixture is obtained. This mixture is able to deposit the pesticidal agents and the polymers on seeds without the need for additional components.

Additionally, polymer emulsions may be useful to prevent the formation of an undesirable moisture barrier surrounding the seeds. Normally, films of latex dispersions containing sufficient amounts of PVA are re-dispersible in water. However, when LMW surfactants are present in seed treatment formulations, their micelles adsorb PVA, depleting the amount of PVA available to envelop the latex, polymer emulsion, or pesticidal agent particles. Thus, a permanent non-redispersible film may be formed which serves as a moisture barrier. A PVA-graft polymer combination forms a protective layer around the latex particles. This protective layer can then form a membrane that inhibits formation of this film or, alternatively, makes it re-dispersible. Thus, a permanent moisture barrier is not formed. Therefore, formulations of this invention may negate or mitigate the adverse effects of LMW surfactants on dispersion stability and seed germination that can be seen in the prior art formulations.

In a preferred embodiment, Dur-O-Set® E-200 (available from Celanese Ltd.) ethylene-vinyl acetate copolymer polymer emulsion may be used.

Wetting Agents and Other Additives

In one embodiment of the invention, the formulations include wetting agents. Most commercially available wetting agents are usable for the purposes of this invention.

The concentration of the wetting agents should be the minimum concentration required to achieve good wetting and film formation. When suitable wetting agents are added, the formulation should wet and form a good film. Normally, suitable wetting agents are functional at 0.2% or less by weight of the total formulation.

In a preferred embodiment, the wetting agent is Tersperse® 4894 (about 88% solids wetting agent), which is made by Huntsman Corporation.

In another embodiment, formulations of this invention contain typical additives used in similar formulations to improve package and handling properties.

Preferred additives include:

organic thickeners, e.g., Kelzan® CC xanthan gum made by CP Kelco;

slip, antiblocking agents, e.g. Michem® Lube 156P slip agent or Michem® Lube 156PFP (a wax emulsion slip agent) available from Michelman Inc.;

defoamers, e.g., Surfynol® 104PG 50% solution of tetramethyl-5-decyne-4,7-diol in propylene glycol defoamer made by Air Products and Chemicals, Inc.;

preservatives, e.g., Kathon® CG/ICP 5-chloro-2-methyl-4-isothiazolin-3-one and 2-methyl-4-isothiazolin-3-one solution in water preservative available from Rohm and Haas Company; and anionic surfactants, e.g., Stepanol® WA-Extra sodium lauryl sulfate anionic surfactant available from Stepan.

Also, a colorant may be added to the disclosed formulations to mark the seeds as coated with pesticides. In a preferred embodiment, Sunsperse® Red 48:2 colorant (from Sun Chemical) is used.

The invention further relates to a method of applying the formulations to seeds. Techniques of seed treatment application are well known to those skilled in the art, and they may be used readily in the context of the present invention. The compositions of the present invention may be applied as a slurry or soak. Film coating and encapsulation may also be used. The coating processes are well known in the art and employ the techniques of film coating, encapsulation, immersion, etc. The method of application of the compositions of the present invention may be varied, and the invention is intended to include any technique that is to be used by one of skill in the art.

The invention further relates to a method of protecting seeds from pests comprising applying to seeds effective amounts of the formulations of the present invention.

The phrase "effective amount" of the formulation means a sufficient amount of the formulation to provide the desired effect. In general, the formulation is employed in amounts that do not inhibit generation of the seeds and do not cause phytotoxic damage to the seeds. The amount of the formulation may vary depending on specific crops and other factors. It is well within the ordinary skill in the art to determine the necessary amount of the formulation.

The two most common application methods are slurry treatment and direct treatment. Specialized seed treatment equipment is available for each of these methods. Direct treaters meter the formulation directly onto the seed without dilution. Slurry treaters meter a water-diluted slurry made from the seed treatment formulation.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The following examples are intended to illustrate the present invention and to teach one of ordinary skill in the art how to make and use the invention. They are not intended to be limiting in any way.

EXAMPLE

Example 1

Preparation of a Seed Treatment Formulation

A formulation for seed treatment was prepared using the following procedure with the amounts by weight percent and by pounds per gallon of the finished product listed below in Table 1.

TABLE 1

| Ingredients | % by Weight in Formulation | lb/gal of Finished Product |
|---|---|---|
| Deionized water | 46.719 | 4.0818 |
| Kelzan ® CC | 0.14 | 0.0122 |
| Michem ® Lube 156P (25% s) | 3.0 | 0.2621 |
| Selvol ® 24-203 (24% s) | 5.0 | 0.4369 |
| Propylene glycol | 5.0 | 0.4369 |
| Kathon ® CG/ICP | 0.14 | 0.0122 |
| Stepanol ® WA-Extra (30% s) | 1.33 | 0.1162 |
| Hexylene glycol | 20.0 | 1.7474 |
| Tersperse ® 2500 (35% s) | 1.0 | 0.0874 |
| Tersperse ® 4894 (88% s) | 0.20 | 0.0175 |
| Surfynol ® 104PG (50% s) | 0.10 | 0.00874 |
| Metalaxyl (97.0% ai) | 0.907 | 0.0792 |
| Clothianidin (97.5% ai) | 3.01 | 0.2630 |
| Metconazole (97.0% ai) | 0.454 | 0.0397 |
| Dur-O-Set ® E 200 (55% s) | 3.0 | 0.2621 |
| Colorant | 10.0 | 0.8737 |
| Total | 100.0 | 8.737 |

Preparation of a Kelzan® CC Premix

First, a 1.5% xanthan gum premix was prepared by adding deionized water and a preservative to a small mixing tank equipped with a high shear mixer. With the mixer operating at 3000 rpm, the xanthan gum was added and mixed for at least one hour to ensure proper dispersion and hydration of the xanthan gum. The amount of each component added is listed below in Table 2.

TABLE 2

| Ingredients | Weight % in Premix | Weight % in Product |
|---|---|---|
| Deionized water | 97.0 | 9.053 |
| Kelzan ® CC | 1.50 | 0.140 |
| Kathon ® CG/ICP | 1.50 | 0.140 |
| Total | 100.0 | 9.333 |

Preparation of a Metalaxyl/Metconazole Solution

Next, a metalaxyl and metconazole solution was prepared. Propylene glycol and hexylene glycol were added to a mixing tank equipped with a mixer. While mixing at a rate sufficient to maintain a vortex, metalaxyl and metconazole were added. The solution was mixed until it was clear and homogeneous. Optionally, the solution may be heated to 40° C. to accelerate the dissolution rate, but the temperature of the solution should not exceed 50° C. The amount of each component added is listed below in Table 3.

TABLE 3

| Ingredients | Weight % in Premix | Weight % in Product |
|---|---|---|
| Metalaxyl (97.0% ai) | 3.44 (3.34% ai) | 0.907 |
| Metconazole (97.0% ai) | 1.72 (1.67% ai) | 0.454 |
| Propylene glycol | 18.97 | 5.00 |
| Hexylene glycol | 75.87 | 20.00 |
| Total | 100.0 | 26.361 |

Preparation of a Clothianidin Slurry

A clothianidin slurry was prepared. Deionized water was added to a mixing tank equipped with a high shear mixer. While mixing at a rate to maintain a vortex, the graft copolymer, wetting agent, and defoamer were added. The mixture was blended for 10 minutes or until it was homogeneous. Next, part of the xanthan gum premix was added and mixed for 20 minutes or until it was homogeneous. The mixer rate was then increased to provide a high shear and vortex, while clothianidin was gradually added. The slow rate of adding clothianidin avoided powder accumulation at the surface. The slurry was mixed for an additional 20 minutes or until the clothianidin was completely dispersed. Optionally, the slurry can be recirculated through an in-line high-speed mixer to facilitate the dispersion process. The amounts of each component are listed below in Table 4.

TABLE 4

| Ingredients | Weight % in Mill Base | Weight % in Product |
|---|---|---|
| Deionized water | 48.96 | 3.28 |
| Tersperse ® 2500 | 1.49 | 0.10 |
| Tersperse ® 4894 | 0.30 | 0.020 |
| Surfynol ® 104PG-50 | 0.15 | 0.010 |

TABLE 4-continued

| Ingredients | Weight % in Mill Base | Weight % in Product |
|---|---|---|
| Kelzan ® CC 1.5% Premix | 4.18 | 0.28 |
| Clothianidin | 44.92 (43.8% ai) | 3.01 |
| Total | 100.0 | 6.70 |

The clothianidin slurry was then milled to the target median particle size using a small media mill equipped with 0.8 to 1.0 mm ceramic media. For example, zirconium silicate or oxide may be used. Any equivalent small media mill may be used that can achieve the desired particle size.

Preparation of the Finished Product

Finally, the finished product was prepared. Deionized water was added to the main blending tank equipped with a high shear mixer. While set at a rate to maintain a vortex, polyvinyl alcohol was added and mixed until homogeneous or for 15 minutes. The polyvinyl alcohol was completely diluted in order to prevent the PVA from precipitating. While mixing, the graft copolymer, wetting agent, and defoamer were added to the tank. Then the slip agent and polymer emulsion were added to the tank.

The mixer rate was then increased to provide a high shear and vortex. The clothianidin slurry was slowly added to the tank over a period of at least 15 minutes. Next, the metalaxyl and metconazole solution was slowly added to the tank. The mixture was agitated at high shear for at least 15 minutes.

While the mixer was running at low shear with a vortex, the sodium lauryl sulfate anionic surfactant and the colorant were added. The mixture was then mixed for 30 minutes or until homogeneous. Finally, the xanthan gum premix was added and mixed until the formulation was homogeneous. Additional water may be added to adjust the viscosity, if necessary. The amount of each component added is listed below in Table 5.

TABLE 5

| Ingredients | Weight % |
|---|---|
| Deionized water | 34.386 |
| Selvol ® 24-203 | 5.0 |
| Tersperse ® 2500 | 0.90 |
| Tersperse ® 4894 | 0.18 |
| Surfynol ® 104PG-50 | 0.090 |
| Michem ® Lube 156P | 3.0 |
| Dur-O-Set ® E-200 | 3.0 |
| Clothianidin Slurry | 6.70 |
| Metconazole/Metalaxyl Solution | 26.361 |
| Stepanol ® WA-Extra | 1.33 |
| Sunsperse ® Red 48:2 | 10.0 |
| Kelzan ® CC 1.5% Premix | 9.053 |
| Total | 100.0 |

Example 2

Preparation of a Seed Treatment Formulation

A formulation for seed treatment was prepared using the following procedure with the amounts by weight percent and by pounds per gallon of the finished product listed below in Table 6.

TABLE 6

| Ingredients | % by Weight in Formulation | lb/gal of Finished Product |
|---|---|---|
| Deionized water | 59.716 | 5.2550 |
| Kelzan ® CC | 0.200 | 0.0176 |
| Michem ® Lube 156P (25% s) | 3.167 | 0.2787 |
| Selvol ® 24-203 (24% s) | 4.356 | 0.3833 |
| Propylene glycol | 5.141 | 0.4524 |
| Kathon ® CG/ICP | 0.205 | 0.0180 |
| Dow Corning ® FG-10 Antifoam | 0.079 | 0.0070 |
| Hexylene glycol | 5.014 | 0.4412 |
| Trimethylolpropane | 1.110 | 0.0977 |
| Urea | 6.335 | 0.5575 |
| Tersperse ® 2500 (35% s) | 1.031 | 0.0907 |
| Tersperse ® 4894 (88% s) | 0.182 | 0.0160 |
| Surfynol ® 104PG (50% s) | 0.079 | 0.0070 |
| Metalaxyl (99.0% ai) | 0.905 | 0.0796 |
| Clothianidin (98.8% ai) | 3.022 | 0.2659 |
| Metconazole (98.7% ai) | 0.454 | 0.0400 |
| Dur-O-Set ® E 200 (55% s) | 3.035 | 0.2671 |
| Sunsperse ® Red 48:2 | 5.969 | 0.5253 |
| Total | 100 | 8.80 |

Preparation of a Kelzan® CC Premix

First, a 1.5% xanthan gum premix was prepared by adding deionized water and a preservative to a small mixing tank equipped with a high shear mixer. With the mixer operating at 3000 rpm, the xanthan gum was added and mixed for at least one hour to ensure proper dispersion and hydration of the xanthan gum. The amount of each component added is listed below in Table 7.

TABLE 7

| Ingredients | Weight % in Premix | Weight % in Product |
|---|---|---|
| Deionized water | 96.96 | 12.928 |
| Kelzan ® CC | 1.50 | 0.200 |
| Kathon ® CG/ICP | 1.54 | 0.205 |
| Total | 100 | 13.333 |

Preparation of a Clothianidin/Metalaxyl/Metconazole Slurry

A slurry of the three active ingredients was prepared. Deionized water was added to a mixing tank equipped with a high shear mixer. While mixing at a rate to maintain a vortex, the graft copolymer, wetting agent, antifoam and defoamer were added. The mixture was blended for 10 minutes or until it was homogeneous. Next, part of the xanthan gum premix was added and mixed for 20 minutes or until it was homogeneous. The mixer rate was then increased to provide a high shear and vortex, while clothianidin, metalaxyl, and metconazole were gradually added. The slow rate of adding the solid materials avoided powder accumulation at the surface. The slurry was mixed for an additional 20 minutes or until the solid active ingredients were completely dispersed. Optionally, the slurry can be recirculated through an in-line high speed mixer to facilitate the dispersion process. The amount of each component added is listed below in Table 8.

TABLE 8

| Ingredients | Weight % in Mill Base | Weight % in Product |
|---|---|---|
| Deionized water | 43.44 | 3.910 |
| Tersperse ® 2500 | 2.00 | 0.180 |
| Tersperse ® 4894 | 0.50 | 0.045 |
| Surfynol ® 104PG-50 | 0.50 | 0.045 |
| Dow Corning ® FG-10 Antifoam | 0.88 | 0.079 |

TABLE 8-continued

| Ingredients | Weight % in Mill Base | Weight % in Product |
|---|---|---|
| Kelzan ® CC 1.5% Premix | 4.00 | 0.360 |
| Metalaxyl (99.0% ai) | 10.06 | 0.905 |
| Clothianidin (98.8% ai) | 33.58 | 3.022 |
| Metconazole (98.7% ai) | 5.04 | 0.454 |
| Total | 100 | 9.000 |

The slurry was then milled to the target median particle size using a small media mill equipped with 0.8 to 1.0 mm ceramic media. For example, zirconium silicate or oxide may be used. Any equivalent small media mill may be used that can achieve the desired particle size.

Preparation of the Finished Product

Finally, the finished product was prepared. Deionized water was added to the main blending tank equipped with a high shear mixer. While set at a rate to maintain a vortex, polyvinyl alcohol was added and mixed until homogeneous or for 15 minutes. The polyvinyl alcohol was completely diluted in order to prevent the PVA from precipitating. While mixing, the propylene glycol, hexylene glycol, trimethylolpropane, urea, and the remaining graft copolymer, wetting agent, and defoamer were added to the tank. Then the slip agent and polymer emulsion were added to the tank.

The mixer rate was then increased to provide a high shear and vortex. The clothianidin/metalaxyl/metconazole slurry was slowly added to the tank over a period of at least minutes. The mixture was agitated at high shear for at least 15 minutes.

While the mixer was running at low shear with a vortex, the colorant was added. The mixture was then mixed for 30 minutes or until homogeneous. Finally, the remainder of the xanthan gum premix was added and mixed until the formulation was homogeneous. Additional water may be added to adjust the viscosity, if necessary. The amount of each component added is listed below in Table 9.

TABLE 9

| Ingredients | Weight % |
|---|---|
| Deionized water | 42.878 |
| Selvol ® 24-203 | 4.356 |
| Propylene glycol | 5.141 |
| Hexylene glycol | 5.014 |
| Trimethylolpropane | 1.110 |
| Urea | 6.335 |
| Tersperse ® 2500 | 0.851 |
| Tersperse ® 4894 | 0.137 |
| Surfynol ® 104PG-50 | 0.034 |
| Michem ® Lube 156P | 3.167 |
| Dur-O-Set ® E-200 | 3.035 |
| Clothianidin/Metalaxyl/Metconazole Slurry | 9.000 |
| Sunsperse ® Red 48:2 | 5.969 |
| Kelzan ® CC 1.5% Premix | 12.973 |
| Total | 100 |

Example 3

Preparation of a Seed Treatment Formulation

A formulation for seed treatment was prepared using the following procedure with the amounts by weight percent and by pounds per gallon of the finished product listed below in Table 10.

TABLE 10

| Ingredients | % by Weight in Formulation | lb/gal of Finished Product |
|---|---|---|
| Deionized water | 66.731 | 6.0389 |
| Kelzan ® CC | 0.180 | 0.0163 |
| Michem ® Lube 156P (25% s) | 4.400 | 0.3982 |
| Selvol ® 203 (solids) | 2.000 | 0.1810 |
| Propylene glycol | 4.600 | 0.4163 |
| Kathon ® CG/ICP | 0.200 | 0.0181 |
| Trimethylolpropane | 0.960 | 0.0869 |
| Urea | 4.600 | 0.4163 |
| Tersperse ® 2500 (35% s) | 1.300 | 0.1176 |
| Tersperse ® 4894 (88% s) | 0.250 | 0.0226 |
| Surfynol ® 104PG (50% s) | 0.250 | 0.0226 |
| Metalaxyl (99.0% ai) | 1.818 | 0.1645 |
| Clothianidin (97.5% ai) | 9.590 | 0.8679 |
| Metconazole (97.0% ai) | 0.371 | 0.0336 |
| Dur-O-Set ® E 200 (55% s) | 2.750 | 0.2489 |
| Total | 100 | 9.05 |

Preparation of a Selvol® 203 20% Solution

First, a 20% polyvinyl alcohol aqueous solution was prepared. Deionized water was added to a small mixing tank which is capable of heating its contents to at least 100° C. While mixing at a rate to maintain a vortex, the solid polyvinyl alcohol was added to the tank. The mixture was then heated to above 90° C. under continuous mixing until the polyvinyl alcohol was completely dissolved. The mixture was cooled to the ambient temperature. The amount of each component added is listed below in Table 11.

TABLE 11

| Ingredients | Weight % in Premix | Weight % in Product |
|---|---|---|
| Deionized water | 80.00 | 8.00 |
| Selvol ® 203 | 20.00 | 2.00 |
| Total | 100 | 10.00 |

Preparation of a Kelzan® CC Premix

Next, a 1.5% xanthan gum premix was prepared by adding deionized water and preservative to a small mixing tank equipped with a high shear mixer. With the mixer operating at 3000 rpm, the xanthan gum was added and mixed for at least one hour to ensure proper dispersion and hydration of the xanthan gum. The amount of each component added is listed below in Table 12.

TABLE 12

| Ingredients | Weight % in Premix | Weight % in Product |
|---|---|---|
| Deionized water | 96.833 | 12.392 |
| Kelzan ® CC | 1.500 | 0.180 |
| Kathon ® CG/ICP | 1.667 | 0.200 |
| Total | 100 | 12.772 |

Preparation of a Clothianidin/Metalaxyl/Metconazole Slurry

A slurry of the three active ingredients was prepared. Deionized water was added to a mixing tank equipped with a high shear mixer. While mixing at a rate to maintain a vortex, the graft copolymer, wetting agent, and defoamer were added. The mixture was blended for 10 minutes or until it was homogeneous. Next, part of the xanthan gum premix was added and mixed for 20 minutes or until it was homogeneous. The mixer rate was then increased to provide a high shear and vortex, while clothianidin, metalaxyl, and metconazole were gradually added. The slow rate of adding the solid materials avoided powder accumulation at the surface. The slurry was mixed for an additional 20 minutes or until the solid active ingredients were completely dispersed. Optionally, the slurry can be recirculated through an in-line high speed mixer to facilitate the dispersion process. The amount of each component added is listed below in Table 13.

TABLE 13

| Ingredients | Weight % in Mill Base | Weight % in Product |
|---|---|---|
| Deionized water | 43.921 | 10.541 |
| Tersperse ® 2500 | 2.000 | 0.480 |
| Tersperse ® 4894 | 0.500 | 0.120 |
| Surfynol ® 104PG-50 | 0.500 | 0.120 |
| Kelzan ® CC 1.5% Premix | 4.000 | 0.960 |
| Clothianidin (97.5% ai) | 39.958 | 9.590 |
| Metalaxyl (99.0% ai) | 7.575 | 1.818 |
| Metconazole (97.0% ai) | 1.546 | 0.371 |
| Total | 100 | 24.000 |

The slurry was then milled to the target median particle size using a small media mill equipped with 0.8 to 1.0 mm ceramic media. For example, zirconium silicate or oxide may be used. Any equivalent small media mill may be used that can achieve the desired particle size.

Preparation of the Finished Product

Finally, the finished product was prepared. Deionized water was added to the main blending tank equipped with a high shear mixer. While set at a rate to maintain a vortex, the 20% polyvinyl alcohol solution was added and mixed until homogeneous or for 15 minutes. The polyvinyl alcohol solution was completely diluted in order to prevent the PVA from precipitating. While mixing, the propylene glycol, trimethylolpropane, urea, and the remainder of the graft copolymer, wetting agent, and defoamer were added to the tank. Then the slip agent and polymer emulsion were added to the tank.

The mixer rate was then increased to provide a high shear and vortex. The clothianidin/metalaxyl/metconazole slurry was slowly added to the tank over a period of at least 15 minutes. The mixture was agitated at high shear for at least 15 minutes.

While the mixer was running at low shear with a vortex, the remainder of the xanthan gum premix was added and mixed until the formulation was homogeneous. Additional water may be added to adjust the viscosity, if necessary. The amount of each component added is listed below in Table 14.

TABLE 14

| Ingredients | Weight % |
|---|---|
| Deionized water | 35.798 |
| Selvol ® 203 20% solution | 10.000 |
| Propylene glycol | 4.600 |
| Trimethylolpropane | 0.960 |
| Urea | 4.600 |
| Tersperse ® 2500 | 0.820 |
| Tersperse ® 4894 | 0.130 |
| Surfynol ® 104PG-50 | 0.130 |
| Michem ® Lube 156P | 4.400 |
| Dur-O-Set ® E-200 | 2.750 |
| Clothianidin/Metalaxy/Metconazole Slurry | 24.000 |
| Kelzan ® CC 1.5 % Premix | 11.812 |
| Total | 100 |

Example 4

Preparation of a Seed Treatment Formulation

A formulation for seed treatment was prepared using the following procedure with the amounts by weight percent and by pounds per gallon of the finished product listed below in Table 15.

TABLE 15

| Ingredients | % by Weight in Formulation | lb/gal of Finished Product |
|---|---|---|
| Deionized water | 68.204 | 5.8443 |
| Kelzan ® CC | 0.250 | 0.0214 |
| Michem ® Lube 156P (25% s) | 4.400 | 0.3770 |
| Selvol ® 203 (solids) | 1.500 | 0.1285 |
| Propylene glycol | 5.000 | 0.4284 |
| Hexylene glycol | 10.000 | 0.8569 |
| Kathon ® CG/ICP | 0.200 | 0.0171 |
| Tersperse ® 2500 (35% s) | 1.000 | 0.0857 |
| Tersperse ® 4894 (88% s) | 0.200 | 0.0171 |
| Surfynol ® 104PG (50% s) | 0.100 | 0.0086 |
| Metalaxyl (99.0% ai) | 0.586 | 0.0502 |
| Clothianidin (97.5% ai) | 3.405 | 0.2918 |
| Metconazole (97.0% ai) | 0.155 | 0.0133 |
| Sunsperse ® Red 48:2 | 5.000 | 0.4284 |
| Total | 100 | 8.57 |

Preparation of a Selvol® 203 20% Solution

First, a 20% polyvinyl alcohol aqueous solution was prepared. Deionized water was added to a small mixing tank which is capable of heating its content to at least 100° C. While mixing at a rate to maintain a vortex, the solid polyvinyl alcohol was added to the tank. The mixture was then heated to above 90° C. under continuous mixing until the polyvinyl alcohol was completely dissolved. The mixture was cooled to the ambient temperature. The amount of each component added is listed below in Table 16.

TABLE 16

| Ingredients | Weight % in Premix | Weight % in Product |
|---|---|---|
| Deionized water | 80.00 | 6.00 |
| Selvol ® 203 | 20.00 | 1.50 |
| Total | 100 | 7.50 |

Preparation of a Kelzan® CC Premix

Next, a 1.5% xanthan gum premix was prepared by adding deionized water and preservative to a small mixing tank equipped with a high shear mixer. With the mixer operating at 3000 rpm, the xanthan gum was added and mixed for at least one hour to ensure proper dispersion and hydration of the xanthan gum. The amount of each component added is listed below in Table 17.

TABLE 17

| Ingredients | Weight % in Premix | Weight % in Product |
|---|---|---|
| Deionized water | 97.300 | 17.129 |
| Kelzan ® CC | 1.500 | 0.250 |
| Kathon ® CG/ICP | 1.200 | 0.200 |
| Total | 100 | 17.579 |

Preparation of a Metalaxyl/Metconazole Solution

A metalaxyl and metconazole solution was prepared. Propylene glycol and hexylene glycol were added to a mixing tank equipped with a mixer. While mixing at a rate sufficient to maintain a vortex, metalaxyl and metconazole were added. The solution was mixed until it was clear and homogeneous. Optionally, the solution may be heated to 40° C. to accelerate the dissolution rate, but the temperature of the solution should not exceed 50° C. The amount of each component added is listed below in Table 18.

TABLE 18

| Ingredients | Weight % in Premix | Weight % in Product |
|---|---|---|
| Metalaxyl (99.0% ai) | 3.723 | 0.586 |
| Metconazole (97.0% ai) | 0.985 | 0.155 |
| Propylene glycol | 31.764 | 5.000 |
| Hexylene glycol | 63.528 | 10.000 |
| Total | 100 | 15.741 |

Preparation of a Clothianidin Slurry

A clothianidin slurry was prepared. Deionized water was added to a mixing tank equipped with a high shear mixer. While mixing at a rate to maintain a vortex, the graft copolymer, wetting agent, and defoamer were added. The mixture was blended for 10 minutes or until it was homogeneous. Next, part of the xanthan gum premix was added and mixed for 20 minutes or until it was homogeneous. The mixer rate was then increased to provide a high shear and vortex, while clothianidin was gradually added. The slow rate of adding the solid materials avoided powder accumulation at the surface. The slurry was mixed for an additional 20 minutes or until the clothianidin was completely dispersed. Optionally, the slurry can be recirculated through an in-line high-speed mixer to facilitate the dispersion process. The amount of each component added is listed below in Table 19.

TABLE 19

| Ingredients | Weight % in Mill Base | Weight % in Product |
|---|---|---|
| Deionized water | 44.357 | 3.105 |
| Tersperse ® 2500 | 2.000 | 0.140 |
| Tersperse ® 4894 | 0.500 | 0.035 |
| Surfynol ® 104PG-50 | 0.500 | 0.035 |
| Kalzan ® CC 1.5% Premix | 4.000 | 0.280 |
| Clothianidin (97.5% ai) | 48.643 | 3.405 |
| Total | 100 | 7.000 |

The slurry was then milled to the target median particle size using a small media mill equipped with 0.8 to 1.0 mm ceramic media. For example, zirconium silicate or oxide may be used. Any equivalent small media mill may be used that can achieve the desired particle size.

Preparation of the Finished Product

Finally, the finished product was prepared. Deionized water was added to the main blending tank equipped with a high shear mixer. While set at a rate to maintain a vortex, the 20% polyvinyl alcohol solution was added and mixed until homogeneous or for 15 minutes. The polyvinyl alcohol solution was completely diluted in order to prevent the PVA from precipitating. While mixing, the graft copolymer, wetting agent, and defoamer were added to the tank. Then the slip agent was added to the tank.

The mixer rate was then increased to provide a high shear and vortex. The clothianidin slurry was slowly added to the tank over a period of at least 15 minutes. Next, the metalaxyl and metconazole solution was slowly added to the tank. The mixture was agitated at high shear for at least 15 minutes.

The colorant was then added. Finally, the remainder of the xanthan gum premix was added and mixed until the formulation was homogeneous. Additional water may be added to adjust the viscosity, if necessary. The amount of each component added is listed below in Table 20.

TABLE 20

| Ingredients | Weight % |
|---|---|
| Water | 41.970 |
| Selvol ® 203 (20% s) | 7.500 |
| Tersperse ® 2500 | 0.860 |
| Tersperse ® 4894 | 0.165 |
| Surfynol ® 104PG-50 | 0.065 |
| Michem ® Lube 156P | 4.400 |
| Clothianidin Slurry | 7.000 |
| Metalaxyl/Metconazole Solution | 15.741 |
| Sunsperse ® Red 48:2 | 5.000 |
| Kelzan ® CC 1.5% Premix | 17.299 |
| Total | 100 |

Example 5

The formulations of the present invention were subjected to seed safety and efficacy testing. The formulations of the present invention provided for excellent seed safety and effective protection against seed and seedling diseases and insects. Further, the seed treatment reduced dust-off of the active ingredients and inerts from the treated seed. Efficiency was compared to untreated seeds and to commercial seed treatment standards known by those familiar to the seed industry.

Seed Safety

Cool, warm and cold germination tests of treated wheat seed utilizing standard methodologies used in the seed industry were conducted to verify that formulations of the present invention were safe to seed. Germination was measured at 6 months after treating with results shown in Table 21 below. Results across the three tests revealed that the Formulation of Example 2 did not reduce germination, but gave germination values equal to the untreated seed.

TABLE 21

| Treatment | Total Grams A.I./100 KG seed | Cool Test (% Germination) | Warm Test (% Germination) | Cold Test (% Germination) |
|---|---|---|---|---|
| Untreated | — | 99.5 | 98.5 | 94.0 |
| Formulation of Example 2 | 14.5 | 99.0 | 99.0 | 96.75 |
| Formulation of Example 2 | 21.75 | 99.5 | 98.5 | 94.0 |

Winter Wheat germination study

Wheat and Barley seed treated with the same seed treatments were stored for three years after treating. Warm germination tests revealed that the Formulation of Example 2 was seed safe over the three-year storage and was similar to the untreated seed. No negative impact was observed in the germination testing.

TABLE 22

| Treatment | Total Grams A.I./100 KG seed | Barley Warm Test (% Germination) | Wheat Warm Test (% Germination) |
|---|---|---|---|
| Untreated | — | 100 | 90.5 |
| Formulation of Example 2 | 14.5 | 99.5 | 86 |
| Formulation of Example 2 | 21.75 | 100 | 90.5 |

Efficacy Against Seed/Seedling Disease

Test 1

In a field study conducted to assess field performance and seedling protection of the Formulation of Example 2 against *Fusarium pseudograminearum*, inoculum of the pathogen was placed in-furrow with wheat seed at the time of planting. Untreated seed was planted both with and without inoculum to assess the disease impact in stand establishment, seedling vigor (height and plant health rating), and in yield. The study revealed that the Formulation of Example 2 gave significant seedling stand improvement over the Untreated Inoculated treatment, and the product applied at two rates gave equal stand establishment as the Untreated Non-inoculated treatment. Plant height and vigor ratings of the Formulation of Example 2 were also significantly better than the Untreated Inoculated treatment, and equal to the Untreated Non-Inoculated treatment. Final yield assessment of the treatments proved the efficacy of the fungicide protection offered in the Formulation of Example 2 in controlling *Fusarium pseudograminearum* with 11.4-11.7 Bu/A increase over the Untreated Inoculated treatment.

TABLE 23

| Treatment | Total Grams A.I./100 KG seed | # Plants/ sq ft. | Plant Height (cm) | Plant Vigor (0-5) @ 46 DAP | Yield (Bu/A) |
|---|---|---|---|---|---|
| Untreated-Non-inoculated | — | 32 | 72 | 4.33 | 68.7 |
| Untreated-Inoculated | — | 24 | 68 | 3.16 | 58.3 |
| Form. of Ex 2 | 14.5 | 31 | 76 | 4.66 | 69.7 |
| Form. of Ex 2 | 21.75 | 34 | 76 | 4.83 | 70.0 |

Spring Wheat Trial Inoculated with *Fusarium pseudograminearum*

Test 2

The Formulation of Example 2 provided excellent activity against barley loose smut caused by the pathogen, *Ustilago nuda*, in a field trial. Stand establishment across treatments showed no significant differences. Yield data from the study showed Formulation of Example 2 provided a numerical value of 3.16-5.33 Bu/A increase over the untreated barley.

TABLE 24

| Treatment | Total Grams A.I./100 KG seed | Stand Count/ meter row | Smutted Heads/ 20 ft row | Yield (Bu/A) |
|---|---|---|---|---|
| Untreated | — | 24.5 | 21.25 | 62.00 |
| Form. of Ex. 2 | 14.5 | 24.3 | 1.50 | 67.33 |
| Form. of Ex. 2 | 21.75 | 30.5 | 0.75 | 65.16 |

Spring Barley Loose Smut (*Ustilago nuda*) Trial

Efficacy Against Seed/Seedling Insects

Wireworms residing in field soils feed on seed and germinating seedlings causing plant damage resulting in loss in field stand establishment of a crop. In a spring wheat trial conducted where wireworm populations were recognized in the field, untreated wheat stands were significantly inferior to all fungicide, insecticide, or fungicide and insecticide combination treatments. When metalaxyl or metconazole were treated on the seed, 1 plant per 0.25 m$^2$ were significantly added. The clothianidin alone treatment gave 2.7 plants more than the untreated. The formulation of Example 2 at the two rates tested provided the best stand establishment of all treatments evaluated giving a significant 5.2 plant increase over the untreated and significantly better than the individual fungicides or clothianidin alone.

TABLE 25

| Treatment | Total Grams A.I./100 KG Seed | Plant Stand # plants/0.25 m$^2$ |
|---|---|---|
| Untreated | — | 12.8 |
| Metalaxyl | 3 | 13.8 |
| Metconazole | 1.5 | 13.5 |
| Clothianidin | 10 | 15.5 |
| Formulation of Example 2 | 14.5 | 18.0 |
| Formulation of Example 2 | 21.75 | 18.0 |

Spring Wheat Trial. Field soil was naturally infested with wireworms at planting.

Reduction in Dust-Off of Active Ingredients/Inerts from Treated Seed

Measurement of dust retention on treated seed is conducted using the Heubach Dustmeter. Such methodology allows assessment of formulations in retaining active ingredient to the seed coat, eliminating dust in the environment during handling. The Formulation of Example 2 dust values were equal to or less than the untreated seed.

TABLE 26

| Treatment | Total Grams A.I. applied/ 100 KG seed | Average Dust Recovered from Treated Seed (g/100 KG seed) |
|---|---|---|
| Untreated control | 0 | 0.63 |
| Metalaxyl + metconazole premix | 4.5 | 0.47 |
| Metalaxyl + metconazole premix + clothianidin | 35.75 | 0.63 |
| Formulation of Example 2 | 14.5 | 0.53 |
| Formulation of Example 2 | 21.75 | 0.63 |

Heubach Dustmeter measurements of treated Jagger Wheat.

Yield Performance Study

The following table provides yield performance in a winter wheat trial. Aphids were noted as a pest in the field trial. The Formulation of Example 1 provided increased yields by effectively controlling the pest.

TABLE 27

| Treatment | Total Grams A.I. applied/100 KG seed | Yield (Bu/A) |
|---|---|---|
| Untreated | — | 58.2 |
| Formulation of Example 1 | 14.5 | 60.1 |
| Formulation of Example 1 | 21.75 | 67.1 |

Winter Wheat Study. Aphids recognized pest in field study.

The invention claimed is:

1. An aqueous seed treatment formulation comprising, in weight % of the total formulation:
   a) from about 0.2 to about 15% of at least one neonicotinoid insecticide selected from the group consisting of clothianidin, imidacloprid, thiamethoxam, acetamiprid, and thiacloprid;

b) from about 0.2 to about 15% of at least one triazole fungicide selected from the group consisting of bitertanol, bromuconazole, cyproconazole, diclobutrazol, difenoconazole, diniconazole, epoxiconazole, fenbuconazole, fluquinconazole, flutriafol, hexaconazole, imibenconazole, ipconazole, metconazole, prothioconazole, simeconazole, tebuconazole, triadimefon, triadimenol, and triticonazole;
c) from about 0.2 to about 4.0% metalaxyl;
d) from about 0.1 to about 0.45% of at least one comb-branched graft copolymer;
e) from about 0.5 to about 2.5% of at least one polyvinyl alcohol (PVA);
f) from about 25 to about 30% of a blend of propylene glycol and hexylene glycol;
g) from about 0.1 to about 0.3% of at least one preservative;
h) from about 0.1 to about 2.0% of at least one anionic surfactant;
i) from about 0.1 to about 0.25% of at least one organic thickener;
j) from about 0.1 to about 0.25% of at least one nonionic wetting agent;
k) from about 0.1 to about 5.0% of at least one polymer emulsion; and
l) water.

2. The formulation of claim 1 wherein the neonicotinoid insecticide pesticidal agent is clothianidin.

3. The formulation of claim 1 wherein the triazole fungicide is metconazole.

4. The formulation of claim 1 further comprising at least one thickener, wetting agent, defoamer, slip agent, polymer emulsion, preservative, anionic surfactant, or colorant.

5. The formulation of claim 1 wherein the organic thickener is xanthan gum.

6. The formulation of claim 1 wherein the polymer emulsion is an ethylene-vinyl acetate copolymer.

7. The formulation of claim 1 further comprising
a) from about 0.1 to about 0.3% of at least one defoamer;
b) from about 0.1 to about 2.0% of at least one slip agent;
c) from about 0.1 to about 15.0% of at least one colorant; and
d) the balance of the formulation is water to total 100% by weight.

8. The aqueous pesticide formulation of claim 7 comprising
a) about 0.35% of at least one comb-branched graft copolymer;
b) about 1.2% of at least one PVA;
c) about 25.0% of a blend of propylene glycol and hexylene glycol;
d) about 0.14% of at least one preservative;
e) about 0.4% of at least one anionic surfactant;
f) about 0.14% of at least one organic thickener;
g) about 0.176% of at least one nonionic wetting agent;
h) about 0.10% of at least one defoamer;
i) about 0.75% of at least one slip agent;
j) about 3.00% of at least one polymer emulsion; and
k) about 10.0% of at least one colorant; and
l) the balance of the formulation is water to total 100% by weight.

9. An aqueous pesticide formulation comprising, in weight % of the total formulation:
a) from about 1.0 to about 12.0% of clothianidin;
b) from about 0.2 to about 4.0% of metalaxyl;
c) from about 0.1 to about 2.0% of metconazole;
d) from about 0.1 to about 0.45% of at least one comb-branched graft copolymer;
e) from about 0.5 to about 2.5% of at least one polyvinyl alcohol (PVA);
f) from about 5.0 to about 30.0% of a blend of propylene glycol and hexylene glycol;
g) from about 0.1 to about 0.3% of at least one preservative;
h) from about 0.1 to about 2.0% of at least one anionic surfactant;
i) from about 0.1 to about 0.25% of at least one organic thickener;
j) from about 0.1 to about 0.25% of at least one nonionic wetting agent;
k) from about 0.1 to about 0.3% of at least one defoamer;
l) from about 0.1 to about 2.0% of at least one slip agent;
m) from about 0.1 to about 5.0% of at least one polymer emulsion;
n) from about 0.1 to about 15.0% of at least one colorant; and
o) the balance of the formulation is water to total 100% by weight.

10. An aqueous pesticide formulation comprising, in weight % of the total formulation:
a) about 3.01% of clothianidin technical, which has 97.5% active ingredient;
b) about 0.907% of metalaxyl technical, which has 97.0% active ingredient;
c) about 0.454% of metconazole technical, which has 97.0% active ingredient;
d) about 0.35% of at least one comb-branched graft copolymer;
e) about 1.2% of at least one PVA;
f) about 25.0% of a blend of propylene glycol and hexylene glycol;
g) about 0.14% of at least one preservative;
h) about 0.4% of at least one anionic surfactant;
i) about 0.14% of at least one organic thickener;
j) about 0.176% of at least one nonionic wetting agent;
k) about 0.10% of at least one defoamer;
l) about 0.75% of at least one slip agent;
m) about 3.00% of at least one polymer emulsion;
n) about 10.0% of at least one colorant; and
o) the balance of the formulation is water to total 100% by weight.

11. A method of preparing the formulation of claim 1 comprising:
a) preparing a thickener pre-mix;
b) preparing a metconazole and metalaxyl mixture;
c) preparing a clothianidin slurry; and
d) combining the thickener pre-mix, metconazole and metalaxyl mixture, and clothianidin slurry.

12. The formulation of claim 2 wherein the clothianidin is from 1.0 to 12%.

13. The formulation of claim 3 wherein the metconazole is from 0.2 to 2.0%.

* * * * *